US012788448B2

(12) United States Patent
Chun et al.

(10) Patent No.: US 12,788,448 B2
(45) Date of Patent: Nov. 10, 2026

(54) PERCUTANEOUS POSTERIOR FIXATION

(71) Applicant: NuVasive, Inc., San Diego, CA (US)

(72) Inventors: Hayden H. Chun, San Diego, CA (US); Matthew Tobias Jacobs, San Diego, CA (US)

(73) Assignee: Globus Medical Inc., Audubon, PA (US)

( * ) Notice: Subject to any disclaimer, the term of this patent is extended or adjusted under 35 U.S.C. 154(b) by 45 days.

(21) Appl. No.: 18/584,474

(22) Filed: Feb. 22, 2024

(65) Prior Publication Data

US 2024/0299065 A1 Sep. 12, 2024

Related U.S. Application Data

(60) Provisional application No. 63/450,710, filed on Mar. 8, 2023.

(51) Int. Cl.
*A61B 17/70* (2006.01)
*A61B 17/00* (2006.01)

(52) U.S. Cl.
CPC ...... *A61B 17/7052* (2013.01); *A61B 17/7049* (2013.01); *A61B 2017/00477* (2013.01)

(58) Field of Classification Search
CPC ........................ A61B 17/7049; A61B 17/7052
See application file for complete search history.

(56) References Cited

U.S. PATENT DOCUMENTS 5,429,639 A * 7/1995 Judet .................. A61B 17/7055 403/362
5,487,742 A * 1/1996 Cotrel ................ A61B 17/7052 606/252
5,562,662 A * 10/1996 Brumfield .......... A61B 17/7002 606/279
5,601,552 A * 2/1997 Cotrel ................ A61B 17/7049 24/135 N
5,702,393 A * 12/1997 Pfaifer ............... A61B 17/7049 606/328
5,702,394 A * 12/1997 Henry ................ A61B 17/7049 606/265
6,027,533 A * 2/2000 Olerud ............... A61B 17/7041 606/258
6,368,320 B1 * 4/2002 Le Couedic ....... A61B 17/7049 606/246
7,666,210 B2 * 2/2010 Franck ............... A61B 17/7052 606/250

(Continued)

FOREIGN PATENT DOCUMENTS

FR 2742040 B1 * 1/1998
FR 2771918 A1 * 6/1999 ......... A61B 17/7049

(Continued)

*Primary Examiner* — Jacqueline T Johanas

(57) ABSTRACT

Various implementations include spinal fixation components and related methods. Certain implementations include a tulip rod connector, including: a spinal rod slot having a first engagement direction; a cross-bar slot having a second engagement direction that is distinct from the first engagement direction; and a lock screw slot adjacent to the cross-bar slot, where the tulip rod connector enables locking of both a spinal rod in the spinal rod slot and a cross-bar in the cross-bar slot with a single lock screw action.

15 Claims, 12 Drawing Sheets

(56) References Cited

U.S. PATENT DOCUMENTS

| | | | | |
|---|---|---|---|---|
| 8,262,700 | B2 * | 9/2012 | Cho | A61B 17/7049 606/250 |
| 8,992,575 | B1 * | 3/2015 | Di Lauro | A61B 17/7041 606/253 |
| 9,463,050 | B2 * | 10/2016 | Schwend | A61B 17/705 |
| 9,603,634 | B1 * | 3/2017 | Frankel | A61B 17/7083 |
| 10,874,439 | B2 * | 12/2020 | Fiechter | A61B 17/7049 |
| 2005/0113831 | A1 * | 5/2005 | Franck | A61B 17/7052 606/246 |
| 2005/0149019 | A1 * | 7/2005 | Sasing | A61B 17/7049 606/279 |
| 2007/0083201 | A1 * | 4/2007 | Jones | A61B 17/7049 606/252 |
| 2007/0213721 | A1 * | 9/2007 | Markworth | A61B 17/7052 606/914 |
| 2007/0213723 | A1 * | 9/2007 | Markworth | A61B 17/7049 606/914 |
| 2008/0021456 | A1 * | 1/2008 | Gupta | A61B 17/7049 606/250 |
| 2009/0099604 | A1 * | 4/2009 | Cho | A61B 17/7049 606/250 |
| 2012/0232593 | A1 * | 9/2012 | Predick | A61B 17/7049 606/276 |
| 2014/0277145 | A1 * | 9/2014 | Reitblat | A61B 17/7086 606/250 |
| 2014/0277146 | A1 * | 9/2014 | Li | A61B 17/7052 606/252 |
| 2016/0058478 | A1 * | 3/2016 | Agarwal | A61B 17/7049 606/270 |
| 2017/0128105 | A1 * | 5/2017 | Patrinicola | A61B 17/7043 |
| 2017/0265904 | A1 * | 9/2017 | Wolfe | A61B 17/7043 |
| 2018/0049778 | A1 * | 2/2018 | Lemerovich | A61B 17/7032 |
| 2018/0344359 | A1 * | 12/2018 | Fiechter | A61B 17/7049 |
| 2019/0125416 | A1 * | 5/2019 | Abe | A61B 17/7034 |
| 2020/0146728 | A1 * | 5/2020 | Daniels | A61B 17/7034 |
| 2022/0110662 | A1 * | 4/2022 | LaColla | A61B 17/7044 |
| 2022/0257291 | A1 * | 8/2022 | Van Der Pol | A61B 17/7052 |
| 2023/0129404 | A1 * | 4/2023 | Lengyel | A61B 17/7035 606/250 |
| 2023/0149047 | A1 * | 5/2023 | McCarthy | A61B 17/7053 606/246 |
| 2023/0346433 | A1 * | 11/2023 | McClintock | A61B 17/7079 |

FOREIGN PATENT DOCUMENTS

| | | | | |
|---|---|---|---|---|
| JP | 2001525213 A | * | 12/2001 | A61B 17/7049 |
| WO | WO-9929248 A1 | * | 6/1999 | A61B 17/7049 |
| WO | WO-2021226057 A1 | * | 11/2021 | A61B 17/7077 |

* cited by examiner

PERCUTANEOUS POSTERIOR FIXATION

CROSS-REFERENCE TO RELATED APPLICATION(S)

This present application is a non-provisional application and claims priority to provisional application No. 63/450,710 filed on Mar. 8, 2023, which is incorporated by reference herein in its entirety for all purposes.

TECHNICAL FIELD

This disclosure generally relates to medical devices. More particularly, the disclosure relates to the field of spinal surgery and spinal fixation devices.

BACKGROUND

Percutaneous posterior spinal fixation procedures can provide significant health benefits and/or relief for patients suffering from a variety of spinal malformities. However, certain conventional approaches are unduly invasive and/or complicated.

SUMMARY

The needs above, as well as others, are addressed by embodiments of spinal rod connectors (also called tulip rod connectors), apparatuses, spinal fixation systems, and related methods described in this disclosure. All examples and features mentioned below can be combined in any technically possible way.

Certain implementations include a tulip rod connector for a spinal construct, the tulip rod connector including: a spinal rod slot having a first engagement direction; a cross-bar slot having a second engagement direction that is distinct from the first engagement direction; and a lock screw slot adjacent to the cross-bar slot, where the tulip rod connector enables locking of both a spinal rod in the spinal rod slot and a cross-bar in the cross-bar slot with a single lock screw action.

In particular aspects, a method of percutaneous posterior fixation on a patient includes: inserting and connecting a cross-bar across a spinal midline of the patient with incisions on either side of the spinal midline.

Additional particular aspects include a cross-bar for a percutaneous posterior fixation procedure, the cross-bar sized to span across a spinal midline of a patient, the cross-bar having: a body having: a fixation section, and a loading section removably coupled with the fixation section, where the loading section is removable after the fixation section engages a set of tulip rod connectors on opposite sides of the spinal midline of a patient.

Implementations may include one of the following features, or any combination thereof.

In certain examples, the cross-bar slot is oversized relative to the cross-bar to enable at least one of: off-axis positioning of the cross-bar, or engagement with a plurality of distinct cross-bars having distinct outer dimensions.

In particular examples, the spinal rod slot enables a pressure-fit connection between the tulip rod connector and the spinal rod.

In some aspects, the spinal rod slot is defined by a set of snap-fit members.

In certain cases, the cross-bar slot is exposed at a top of the tulip rod connector.

In particular aspects, the tulip rod connector further includes a locking flange for engaging the cross-bar in the cross-bar slot.

In some implementations, the cross-bar slot is closed at a top of the tulip rod connector.

In certain cases, the tulip rod connector further includes a compliant bending zone adjacent to the spinal rod slot and the cross-bar slot.

In some aspects, the compliant bending zone translates at least a portion of a downward force from the single lock screw action at the lock screw slot into a clamping force on the rod slot.

In some implementations, the compliant bending zone is defined by at least one of an aperture or a thinned section.

In certain aspects, the second engagement direction is approximately perpendicular to the first engagement direction.

In particular cases, a body of the tulip rod connector is a monolithic piece of material. The monolithic piece of material can include a unitary piece of metal or composite.

In some implementations, a body of the tulip rod connector includes a plurality of distinct components, including: a main body and a collet at least partially defining the spinal rod slot.

In particular aspects, a width of the spinal rod slot is larger than a width of the cross-bar slot.

In certain cases, the cross-bar slot is non-circular.

In some implementations, the cross-bar slot has a rounded rectangular cross-sectional shape in a direction perpendicular to the second engagement direction.

In particular cases, inserting and connecting the cross-bar is performed without any incision (e.g., external incision) through the spinal midline of the patient.

In certain aspects, inserting and connecting the cross-bar is performed with only two incisions, one on each side of the spinal midline.

In particular implementations, inserting and connecting the cross-bar is performed with a lateral, subcutaneous insertion across the spinal midline.

In some cases, the method further includes: coupling a first tulip rod connector to a first spinal rod on a first side of the spinal midline of the patient, coupling a second tulip rod connector to a second spinal rod on a second side of the spinal midline of the patient, inserting a cross-bar in a first cross-bar slot in the first tulip rod connector, inserting the cross-bar in a second cross-bar slot in the second tulip rod connector, securing the cross-bar with a first lock screw in the first tulip rod connector, and securing the cross-bar with a second lock screw in the second tulip rod connector.

In some aspects, a method further includes coupling a first tulip rod connector to a first spinal rod on a first side of the spinal midline of the patient, the first tulip rod connector including a first cross-bar slot, inserting a cross-bar in a second cross-bar slot in a second tulip rod connector on a second side of the spinal midline of the patient, coupling the second tulip rod connector to a second spinal rod on the second side of the spinal midline of the patient, inserting the cross-bar in the first cross-bar slot in the first tulip rod connector, securing the cross-bar with a first lock screw in the first tulip rod connector, and securing the cross-bar with a second lock screw in the second tulip rod connector.

In particular cases, a method further includes: coupling a first tulip rod connector to a first spinal rod on a first side of the spinal midline of the patient, coupling a cross-bar in a first cross-bar slot in the first tulip rod connector, securing the cross-bar in the first tulip rod connector with a first lock screw, coupling a second tulip rod connector to a second spinal rod on a second side of the spinal midline of the patient, coupling the cross-bar to a second cross-bar slot in the second tulip connector, and securing the cross-bar in the second tulip rod connector with a second lock screw.

In certain implementations, securing the cross-bar in the first tulip rod connector is performed prior to coupling the second tulip rod connector to the second spinal rod on the second side of the spinal midline.

In some aspects, coupling the first tulip rod connector to the first spinal rod and coupling the cross-bar in the first cross-bar slot is performed with a reducer tool.

In particular cases, the reducer tool is configured to engage the first tulip rod connector and the cross-bar in a direction perpendicular to a direction of the first spinal rod.

In certain examples, the reducer tool is configured to pass the cross-bar from the first side of the spinal midline to the second side of the spinal midline. In some examples, the reducer tool includes a reducer tower.

In some cases, the method is performed using a first tulip rod connector on a first side of the spinal midline and a second tulip rod connector on a second side of the spinal midline.

In particular examples, the spinal rod slot of each tulip rod connector enables a pressure-fit connection between the respective tulip rod connector and the spinal rod during the inserting and connecting processes.

In some cases, the method can be used in an initial spinal construction surgery.

In certain cases, the method can be used in a spinal revision surgery.

In particular aspects, the cross-bar has a fixation section with a longitudinal axis aligned with an insertion direction across the spinal midline of the patient.

In some cases, the cross-bar includes a break zone between the fixation section and the loading section for enabling removal of the loading section.

In certain examples, the fixation section has a cylindrical cross-sectional shape.

In particular aspects, the fixation section has a non-cylindrical cross-sectional shape including at least one of an ellipse, a rounded rectangle, or a tapered rectangle.

In some cases, the fixation section is sized to fit in a cross-bar slot in each of the tulip rod connectors with clearance to enable coupling between tulip rod connectors that are misaligned in at least one of an X direction, Y direction, or Z direction.

In particular examples, a tip of the fixation section is tapered or pointed.

In some aspects, the fixation section is both bendable and rotatable.

In certain examples, the fixation section includes a section having a reduced cross-sectional dimension (e.g., bend zone) to aid in at least one of bending or rotating.

Two or more features described in this disclosure, including those described in this summary section, may be combined to form implementations not specifically described herein.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

The details of one or more implementations are set forth in the accompanying drawings and the description below. Other features, objects and benefits will be apparent from the description and drawings, and from the claims.

BRIEF DESCRIPTION OF THE DRAWINGS

FIG. 20 is a flow diagram illustrating processes in a method according to various implementations.

FIG. 21 is a flow diagram illustrating processes in a method according to various additional implementations.

FIG. 22 is a flow diagram illustrating processes in a method according to various implementations.

Figure 1:
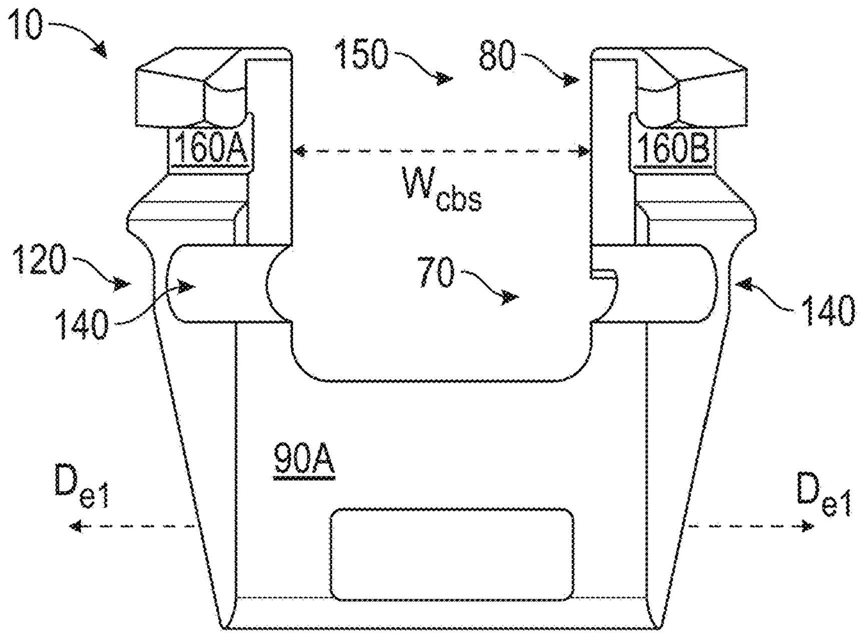
FIG. 1 shows a front view of a tulip rod connector according to various implementations.

It is noted that the drawings of the various implementations are not necessarily to scale. The drawings are intended to depict only typical aspects of the disclosure, and therefore should not be considered as limiting the scope of the implementations. In the drawings, like numbering represents like elements between the drawings.

DETAILED DESCRIPTION

Various implementations include spinal fixation components and related methods. Particular implementations include systems, devices, and methods for a modular, percutaneous posterior fixation system. One embodiment of a system utilizes a tulip head connector implant which provides a connection and/or extension from one rod to another rod through a joining cross-bar and a lock-screw locking mechanism. One approach utilizes a minimally invasive percutaneous approach for posterior spine surgery, including percutaneous delivery of implant components utilizing a combination of extension tube tower instrumentation and rod inserters to assemble the implants in-situ.

In the interest of clarity, not all features of an actual implementation are necessarily described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The devices, related systems, and methods described herein boast a variety of inventive features and components that warrant patent protection, both individually and in combination. It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

This disclosure provides, at least in part, a tulip rod connector for a spinal fixation system. The tulip rod connector can include: a spinal rod slot having a first engagement direction; a cross-bar slot having a second engagement direction that is distinct from the first engagement direction; and a lock screw slot adjacent to the cross-bar slot, where the tulip rod connector enables locking of both a spinal rod in the spinal rod slot and a cross-bar in the cross-bar slot with a single lock screw action. Further implementations include a method of percutaneous posterior fixation on a patient by inserting and connecting a cross-bar across a spinal midline of the patient with incisions on either side of the spinal midline. Additional implementations include a cross-bar for a percutaneous posterior fixation procedure that is sized to engage the tulip rod connector.

The various disclosed implementations can enable a minimally invasive percutaneous spinal fixation procedure. Certain disclosed implementations enable insertion and connection of a cross-bar across a spinal midline of a patient with incisions on either side of the midline. Particular disclosed implementations enable inserting and connecting the cross-bar across the spinal midline without any incision (e.g., external incision) through the spinal midline of the patient. Other disclosed implementations enable inserting and connecting the cross-bar with only two incisions, one on each side of the spinal midline. Further disclosed implementations enable inserting and connecting the cross-bar with a lateral, subcutaneous insertion across the spinal midline.

Commonly labeled components in the drawings are considered to be substantially equivalent components for the purposes of illustration, and redundant discussion of those components is omitted for clarity.

Figure 2:
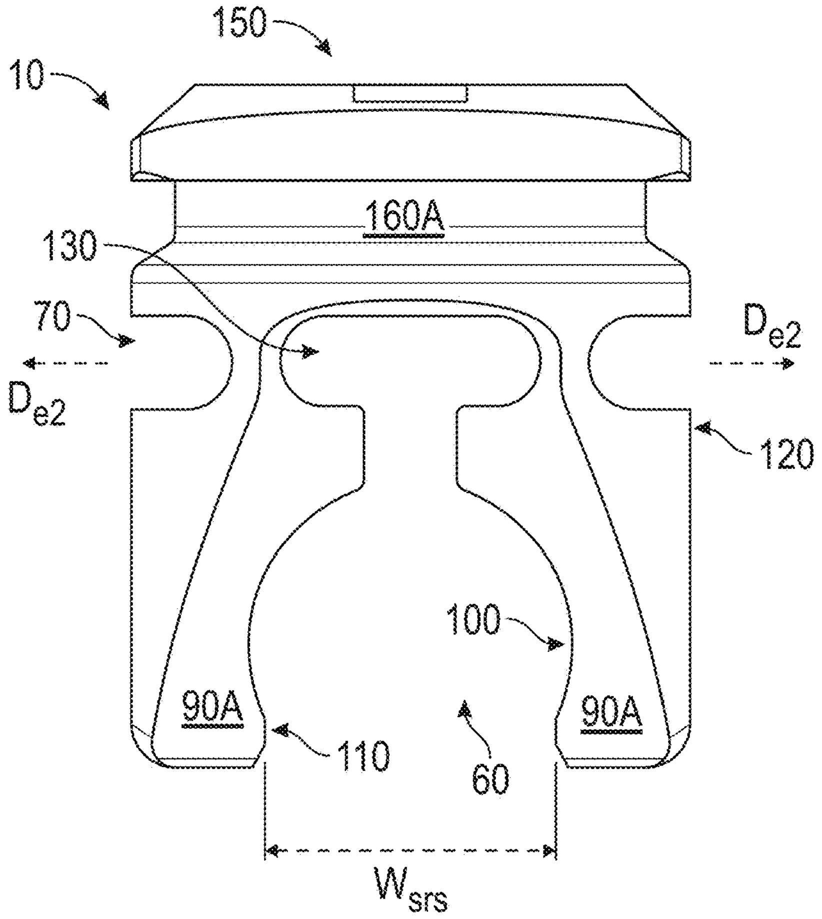
FIG. 2 shows a side view of the tulip rod connector of FIG. 1.
Figure 3:
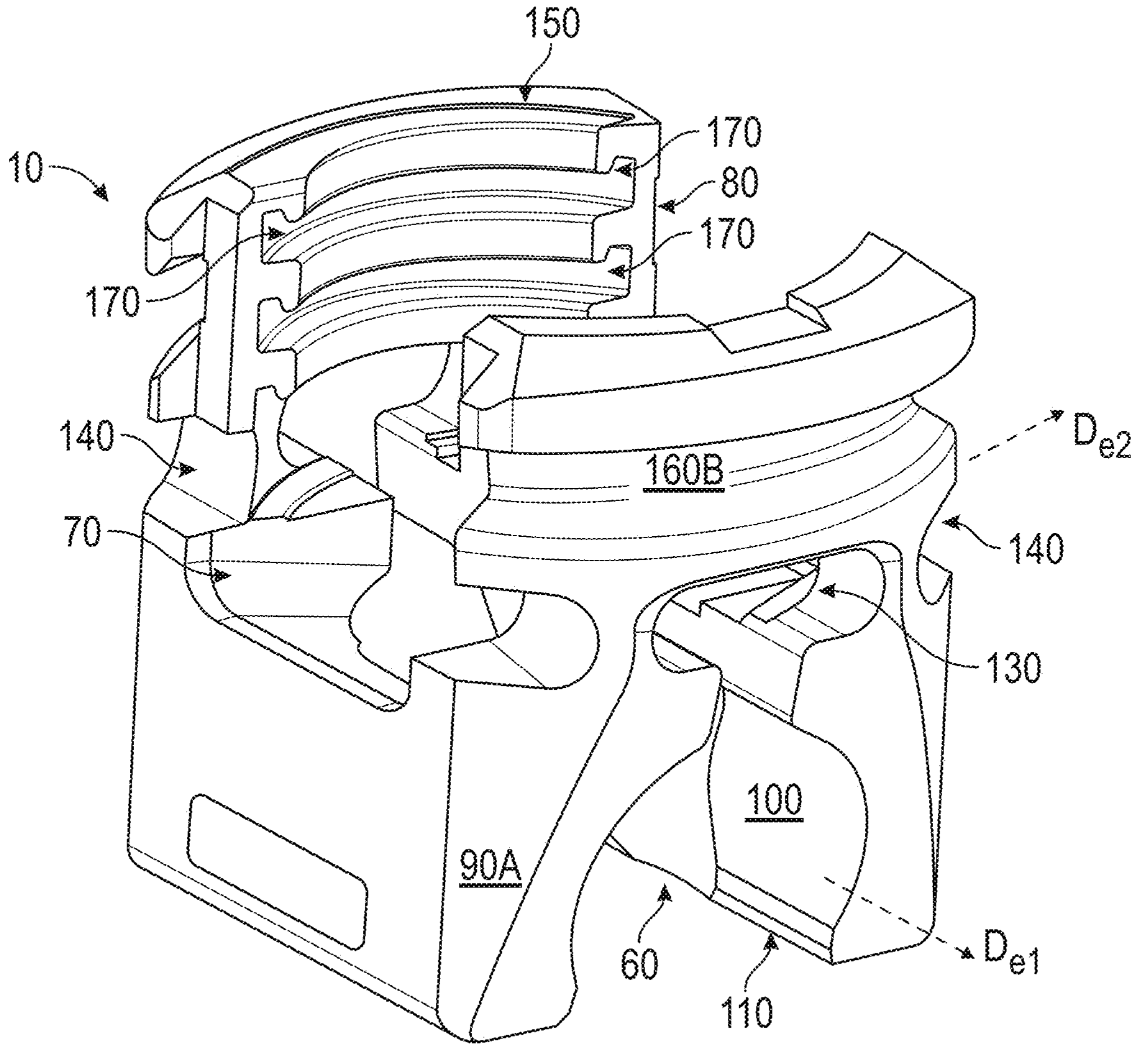
FIG. 3 shows a perspective view the tulip rod connector of FIGS. 1 and 2.
Figure 4:
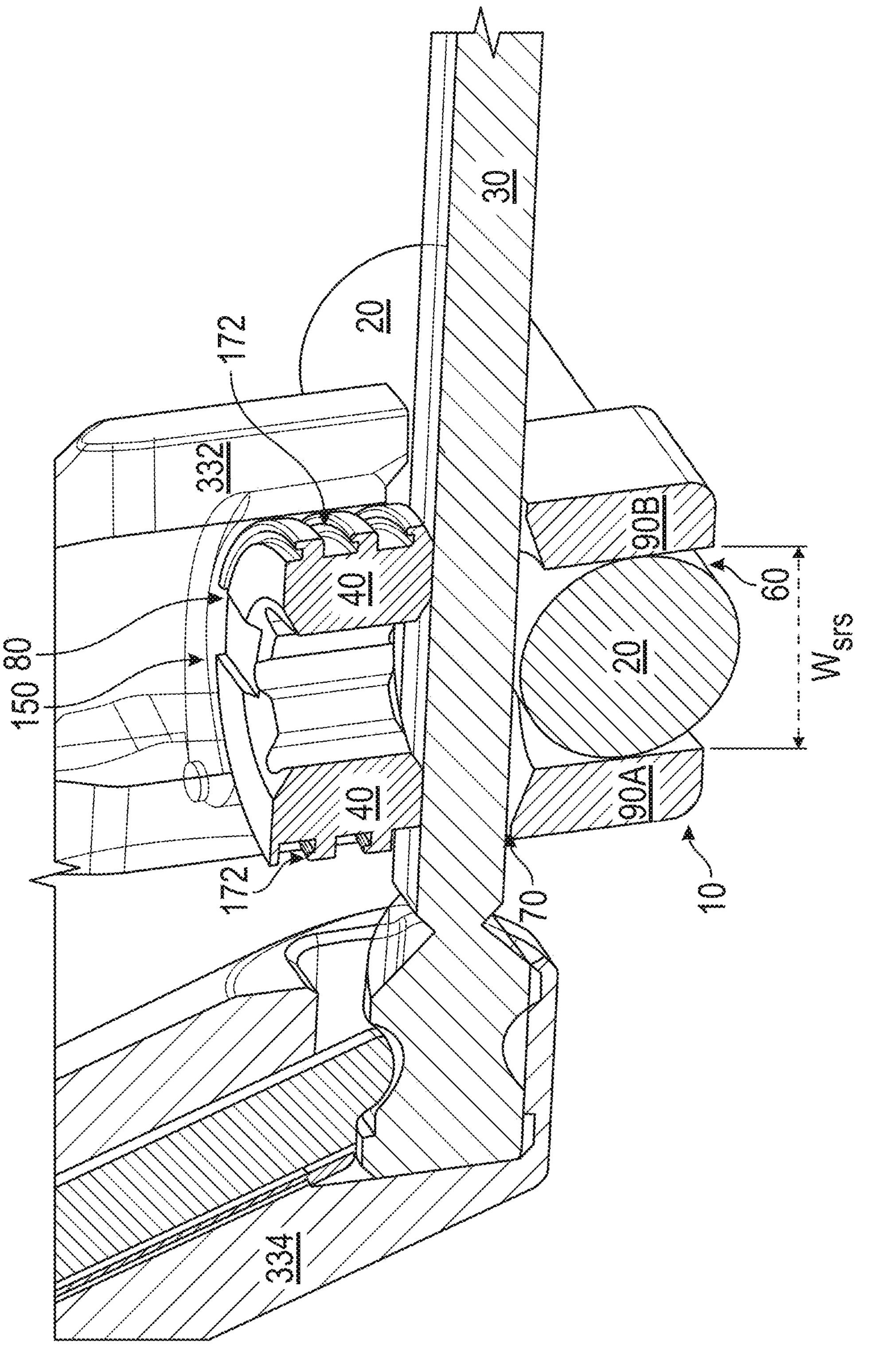
FIG. 4 shows a partial cross-section of the tulip rod connector of FIGS. 1-3 with a cross-bar, spinal rod, and reducer tools.
Figure 5:
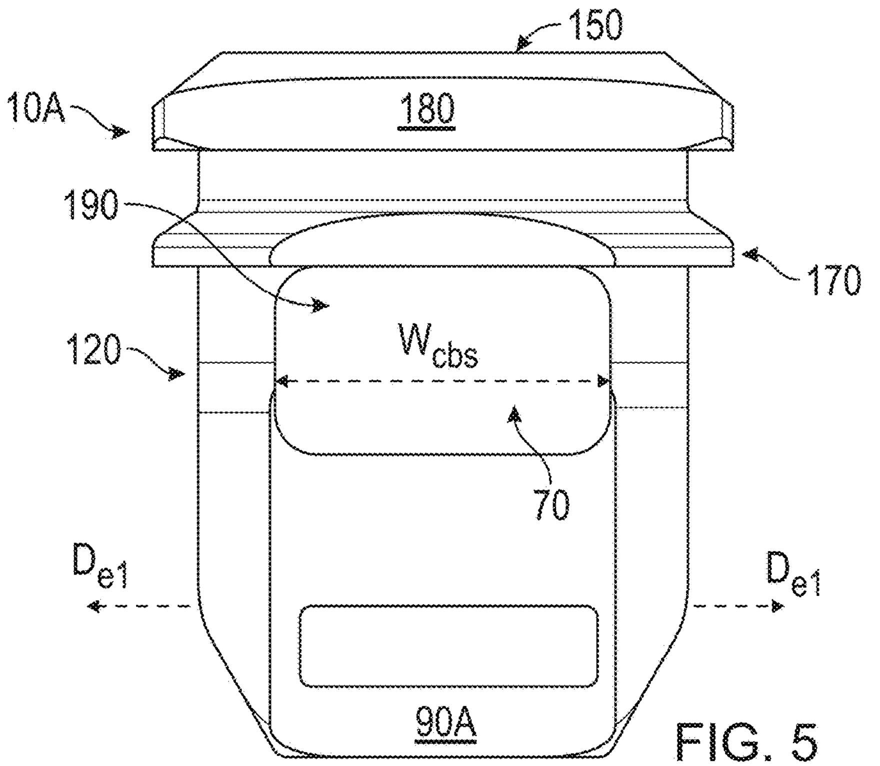
FIG. 5 shows a front view of a tulip rod connector according to various additional implementations.
Figure 6:
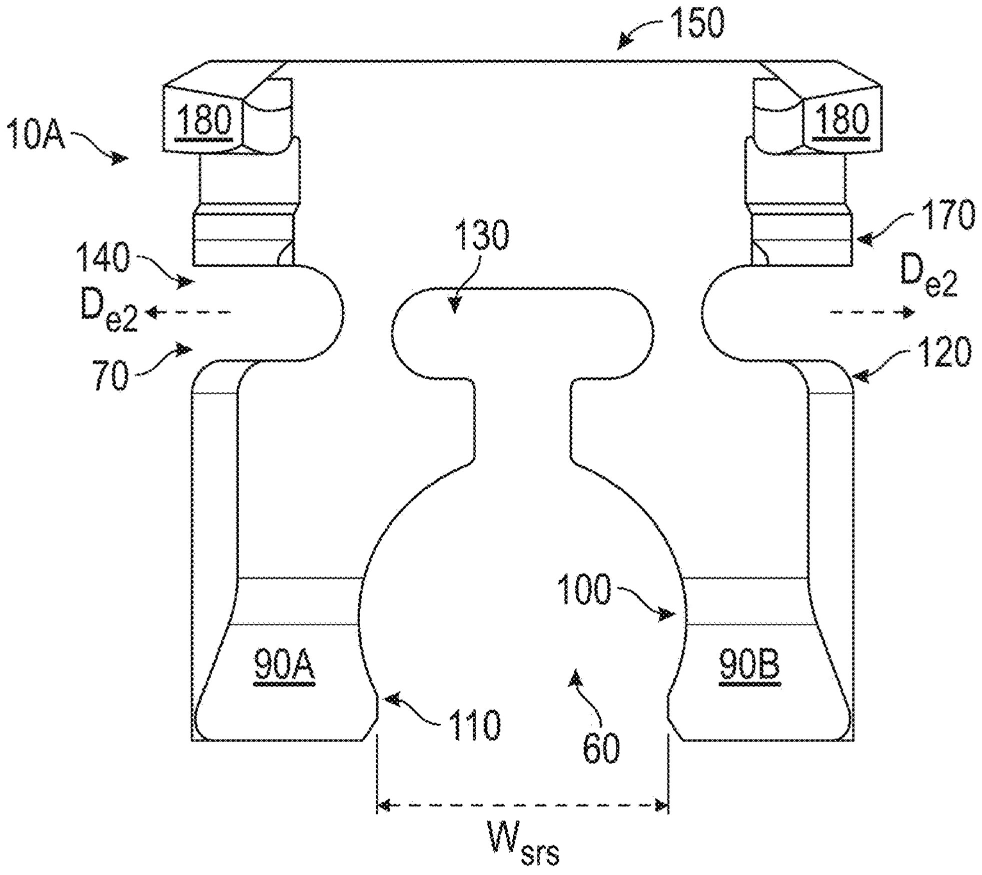
FIG. 6 shows a side view of the tulip rod connector of FIG. 5.
Figure 7:
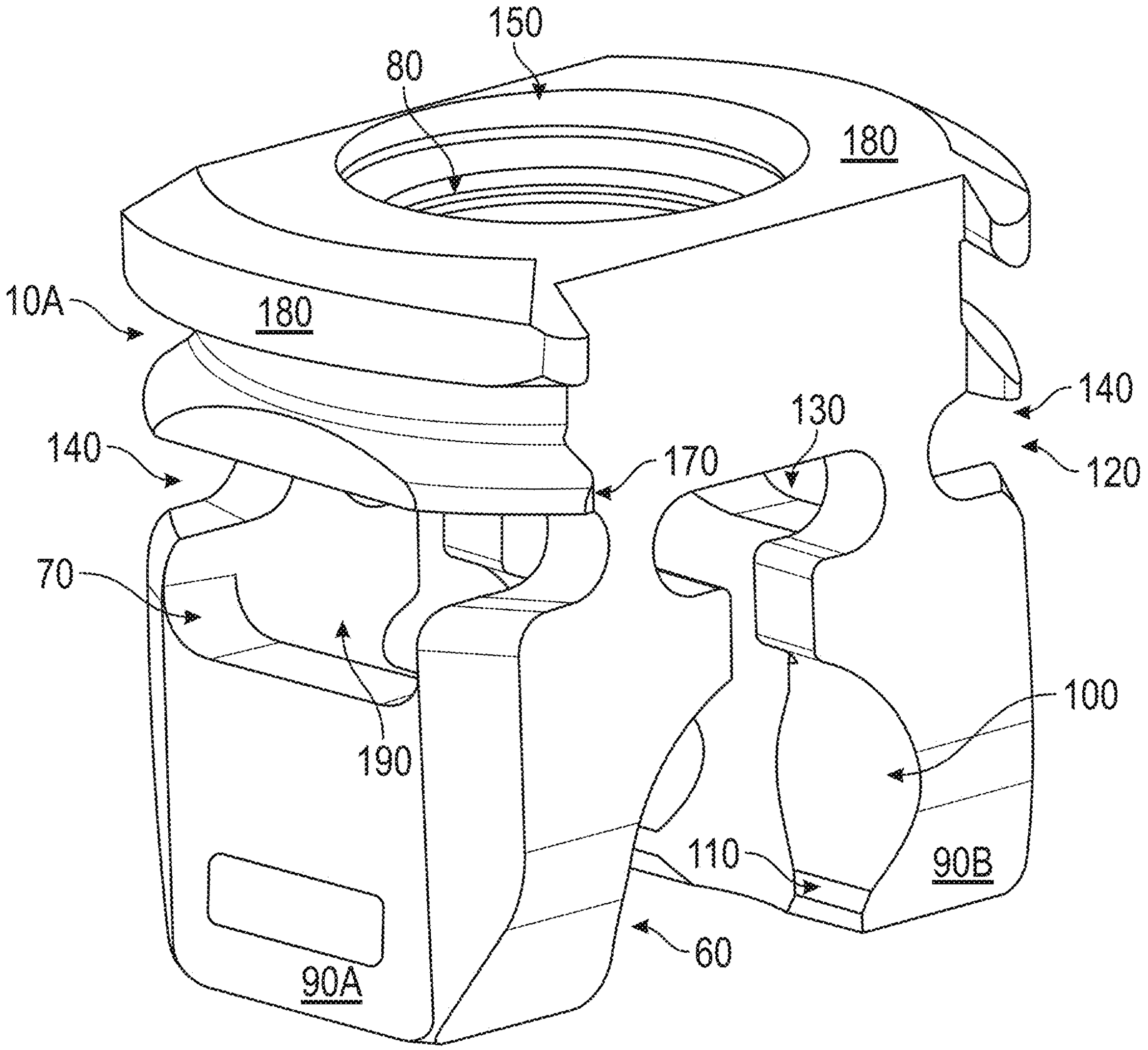
FIG. 7 shows a perspective view the tulip rod connector of FIGS. 5 and 6.
Figure 8:
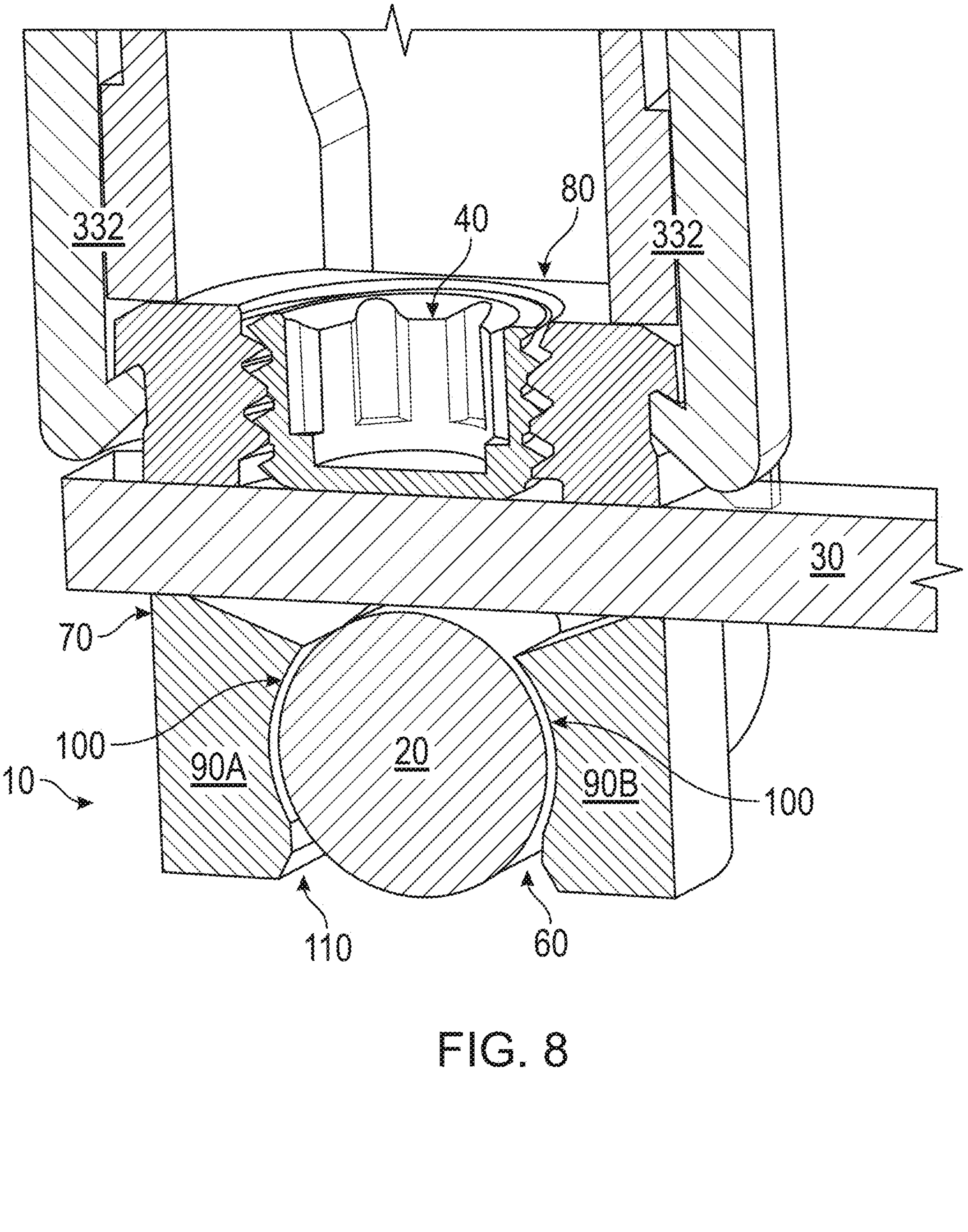
FIG. 8 shows a partial cross-sectional view of the tulip rod connector of FIGS. 5-7 with a cross-bar, spinal rod, and reducer tool.
Figure 9:
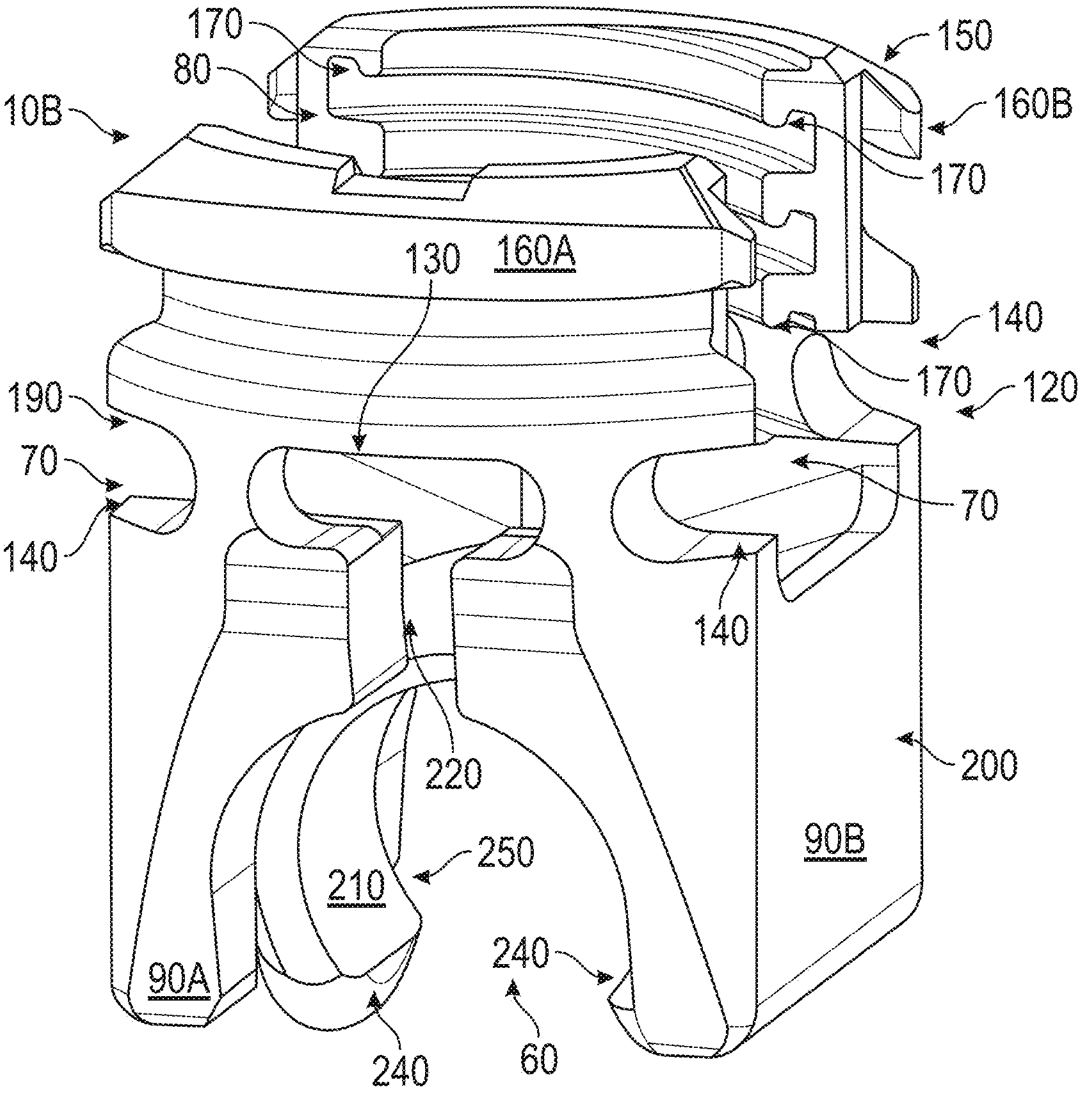
FIGS. 9-13 illustrate side, top, perspective, and cut-away views of a tulip rod connector according to various additional implementations.
Figure 10:
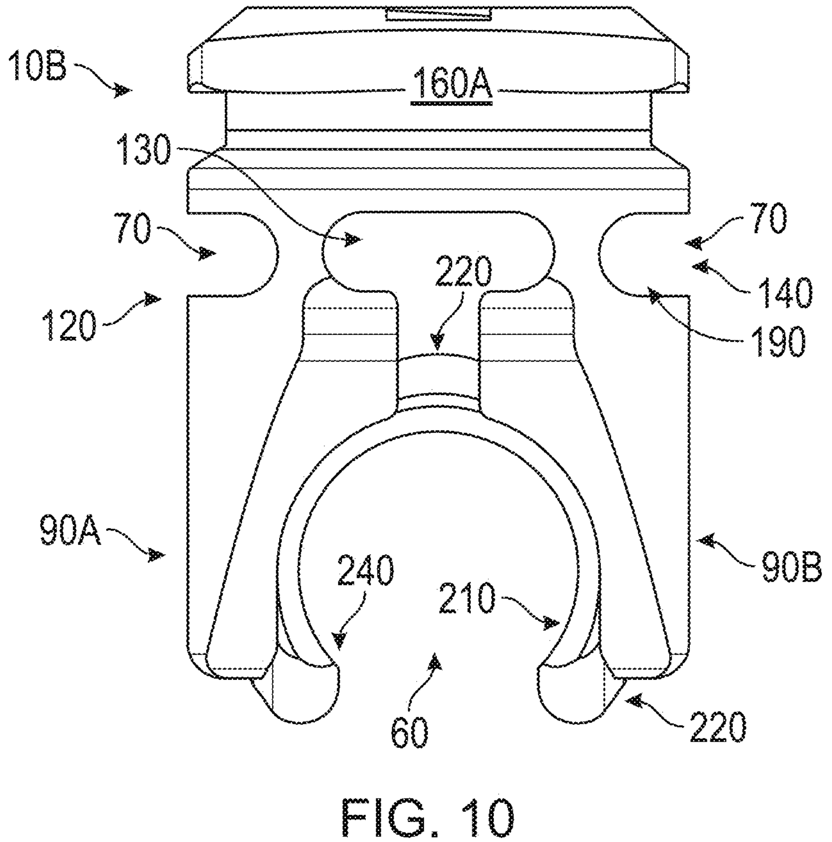
Figure 11:
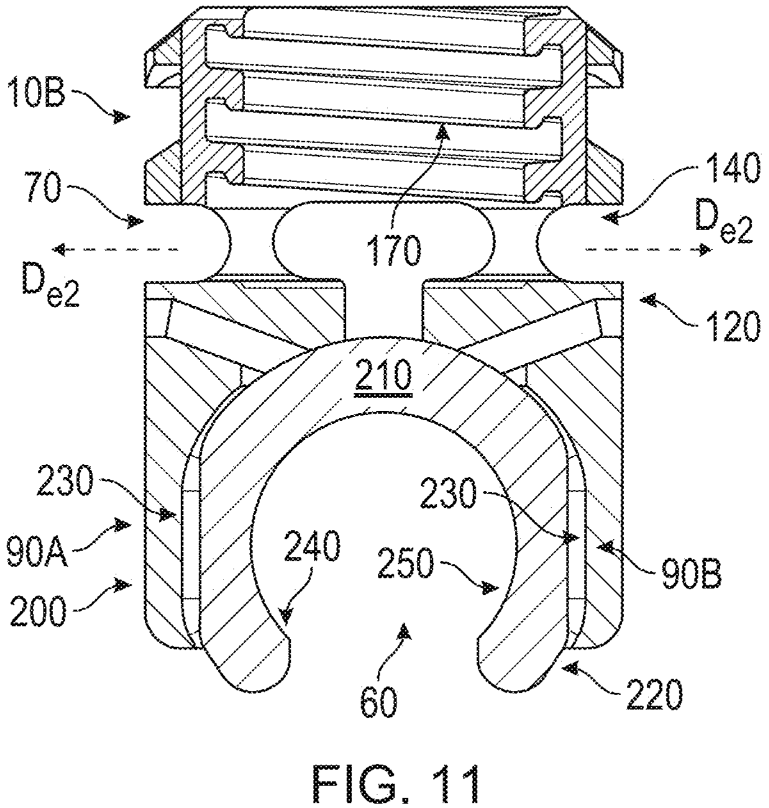
Figure 12:
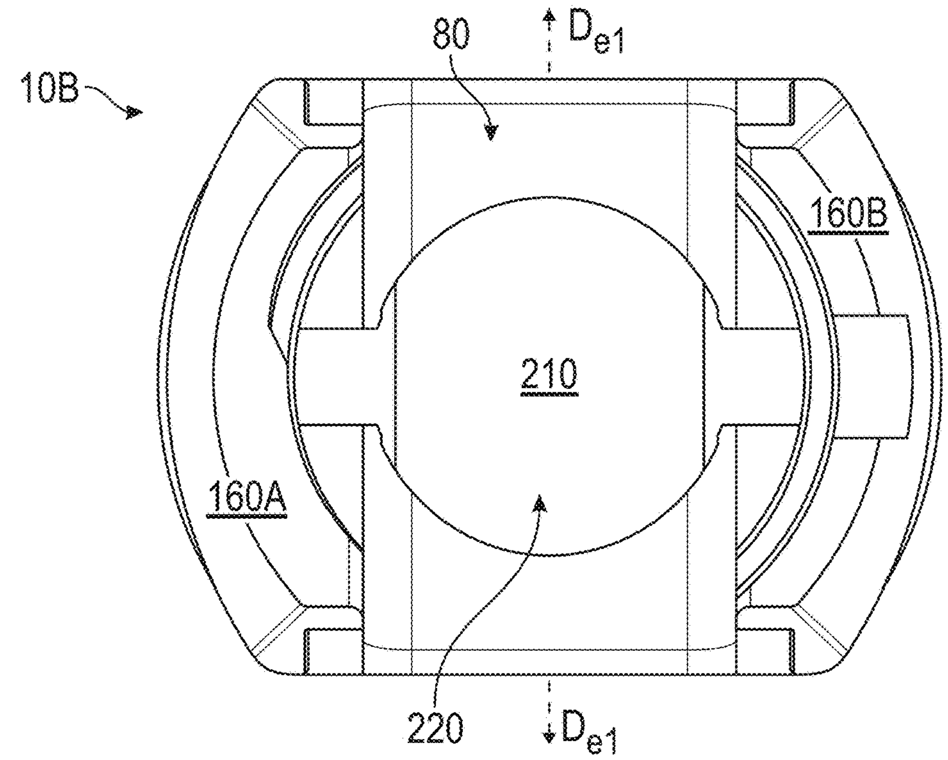
Figure 13:
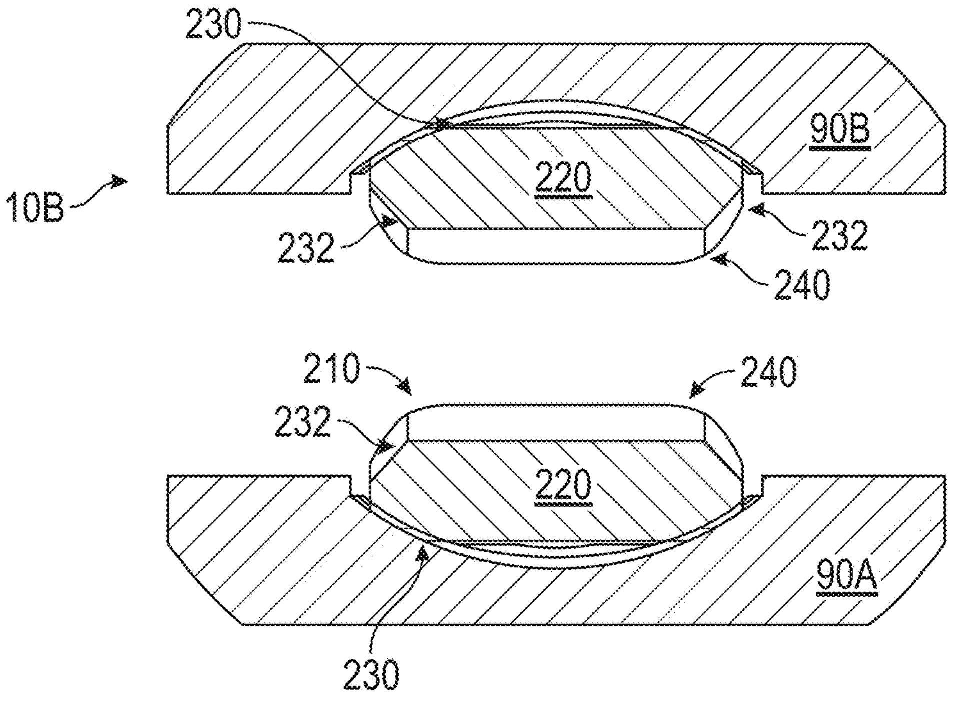
Figure 14:
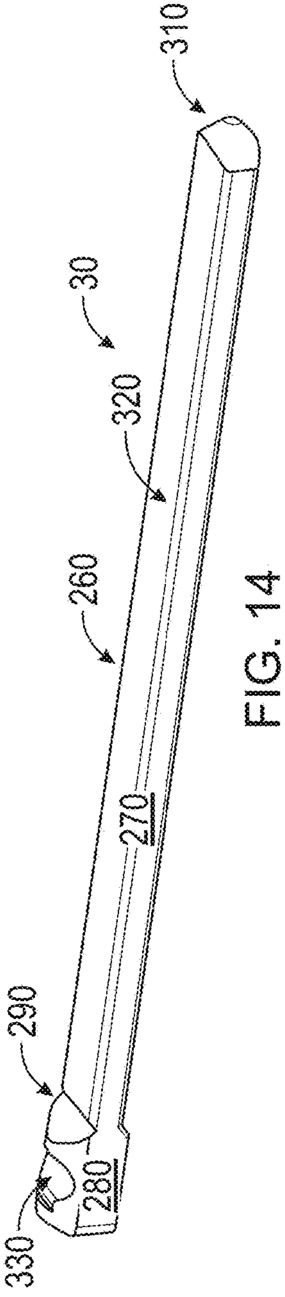
FIGS. 14-17 illustrate perspective, side, top, and end views of a cross-bar according to various implementations.
Figure 15:
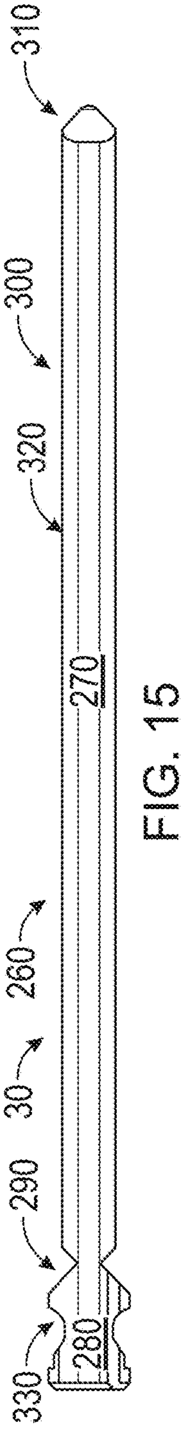
Figure 18:
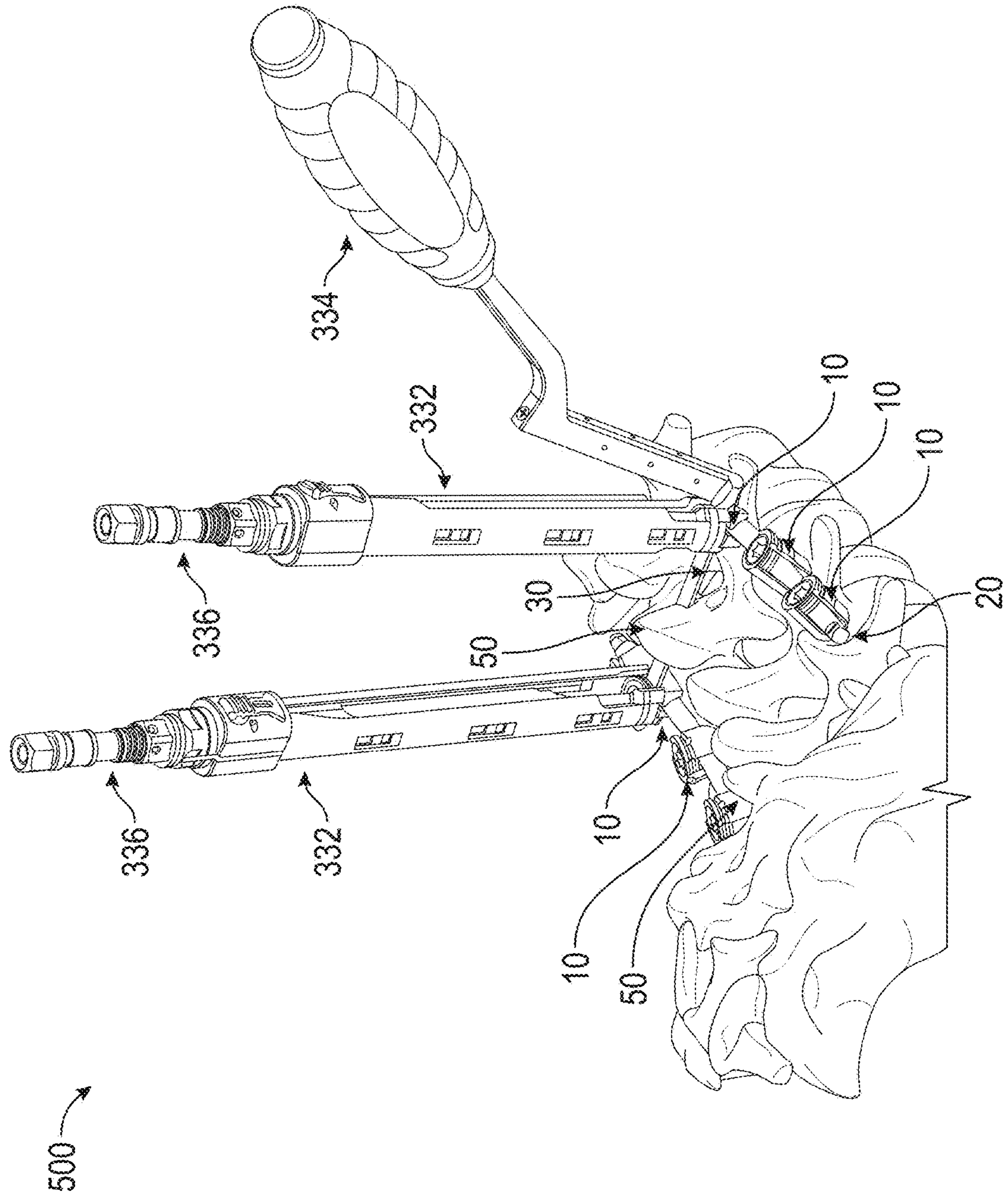
FIG. 18 is a perspective view of a system for assembling a spinal fixation construct, including a depiction of a portion of a patient's spinal midline according to various implementations.
Figure 19:
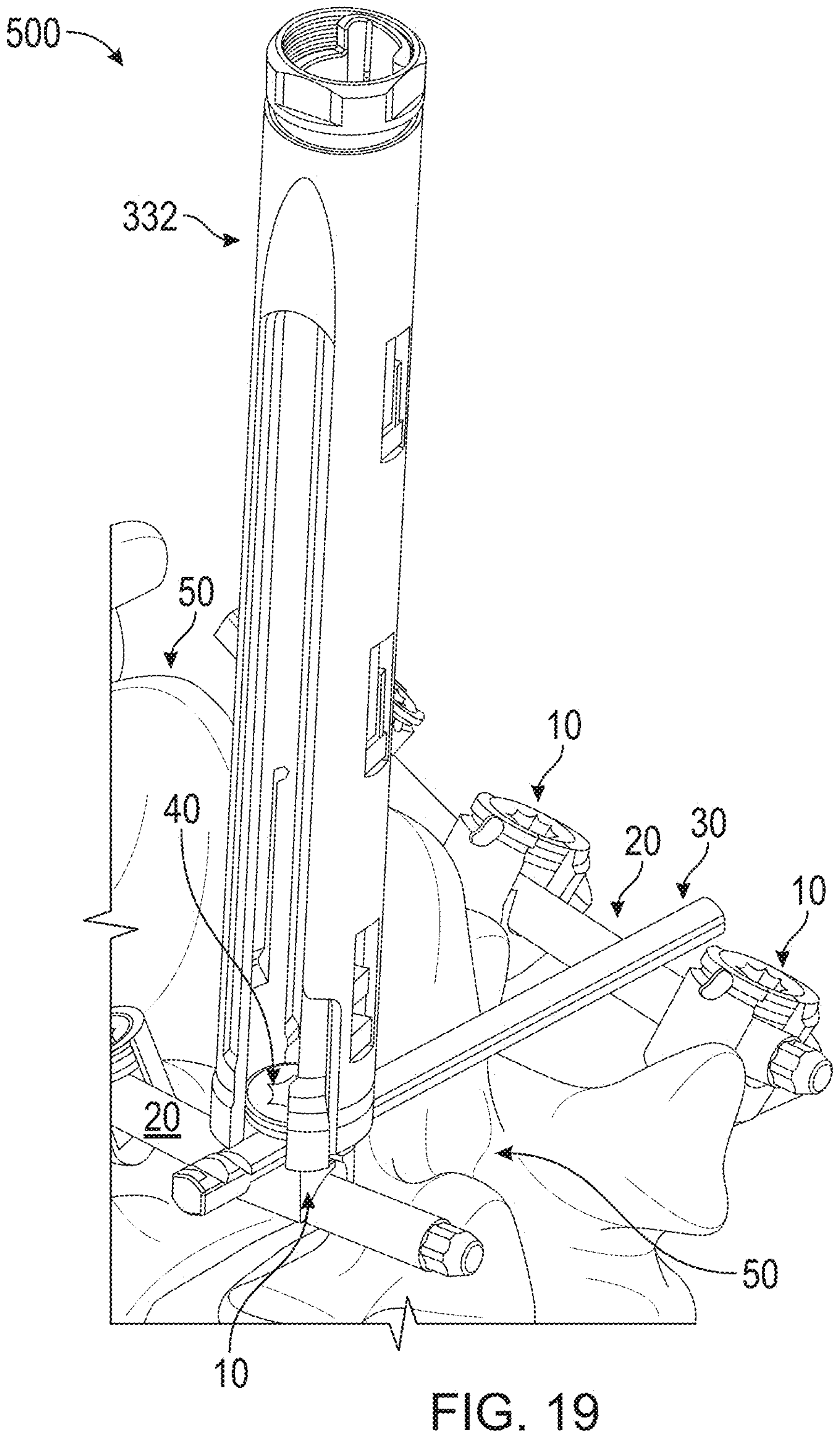
FIG. 19 is a close-up perspective view of a partially completed spinal fixation construct spanning a patient's spinal midline according to various implementations.

FIGS. 1-3 illustrate a tulip rod connector 10 (also called a "connector") for use in a spinal fixation procedure. FIGS. 1, 2, and 3 illustrate a front view, side view, and perspective view, respectively, of the connector 10. FIG. 4 illustrates the connector 10 interfacing with a spinal rod 20, a cross-bar 30, and a lock screw 40. As described further herein with respect to FIG. 4, the tulip rod connector 10 is configured to couple with both a spinal rod 20 and a cross-bar 30 as part of a spinal fixation construct. As is known in the art, a spinal rod 20 extends generally along the spine of a patient, e.g., along one side of a patient's spinal midline. FIGS. 18 and 19 illustrate an apparatus 500 for performing a spinal fixation procedure using the tulip rod connector 10, showing the patient's spinal midline 50 and a cross-bar 30 spanning across that spinal midline 50 between two connectors 10.

Returning to FIGS. 1-3, the connector 10 can include a spinal rod slot 60 with a first engagement direction ($D_{e1}$), and a cross-bar slot 70 with a second, distinct engagement direction ($D_{e2}$). In various implementations, $D_{e1}$ is approximately perpendicular to $D_{e2}$. The spinal rod slot 60 is configured to receive a spinal rod 20, and the cross-bar slot 70 is configured to receive a cross-bar 30 (FIG. 4). In various implementations, a lock screw slot 80 is positioned adjacent to the cross-bar slot 70, and is configured to receive a lock screw 40 (FIG. 4). As described herein and at least partially illustrated in FIG. 4, the connector 10 may be configured to enable locking of both the spinal rod 20 in the spinal rod slot 60 and the cross-bar 30 in the cross-bar slot 70 with a single lock screw action, e.g., by tightening the lock screw 40 to engage complementary threads in the connector 10.

In various implementations, the spinal rod slot 60 enables a pressure-fit connection between the connector 10 and the spinal rod (FIG. 4). In certain cases, the spinal rod slot 60 is defined by a set of snap-fit members 90, e.g., two opposing snap-fit members 90A, 90B that can be sized and/or separated to allow flexion for engaging or disengaging the spinal rod 20. In certain cases, the snap-fit members 90A, 90B include a partially arcuate inner surface 100 that is configured to complement a portion of the arcuate outer surface of the spinal rod 20. In some cases, each snap-fit member 90A includes a lip 110 configured to retain the spinal rod 20 after it is snapped into the slot 60. In additional implementations, the spinal rod slot 60 can be defined by a set of members, e.g., separate members, where at least one of those members is rigid, or fixed, and at least one of the members is compliant (e.g., a snap-fit member). In one example, the spinal rod slot 60 is defined by one snap fit member (e.g., snap-fit member 90A) and an opposing rigid (or, fixed) member.

In some cases, the cross-bar slot 70 is oversized relative to the cross-bar 30 to enable off-axis positioning of the cross-bar 30 and/or engagement with a plurality of distinct cross-bars having distinct outer dimensions. That is, the cross-bar slot 70 can have an inner dimension that is larger than an outer dimension of the cross-bar 30 (as measured perpendicular to $D_{e2}$). In such cases, the cross-bar slot 70 allows the cross-bar 30 to be positioned at angles that deviate from the second engagement direction ($D_{e2}$), e.g., by up to 5 degrees, 10 degrees, or 15 degrees. Further, in some aspects, the cross-bar slot 70 is sized to receive cross-bars of varying sizes (e.g., outer dimensions, or widths), making the connector 10 adaptable for spinal fixation procedures on patients of differing construct sizes. In certain cases, a width ($W_{cbs}$) of the cross-bar slot 70 is smaller than a width ($W_{srs}$) of the spinal rod slot 60.

In certain aspects, the connector 10 further includes a compliant bending zone 120 that is adjacent to the spinal rod slot 60 and the cross-bar slot 70. The compliant bending zone 120 can be defined by an aperture 130 and/or a thinned section 140 (e.g., a cutout in sidewall(s)) in the connector 10 (thinned relative to neighboring sections). In various implementations, e.g., as illustrated in FIG. 4, the compliant bending zone 120 translates at least a portion of a downward force from the single lock screw action at the lock screw slot 80 into a clamping force on the spinal rod slot 60. That is, the compliant bending zone 120 enables locking of both the spinal rod 20 and the cross-bar 30 with actuation of the lock screw 40 in the lock screw slot 80. FIG. 4 aids in illustrating this function in the connector 10; as the lock screw 40 is tightened in the lock screw slot 80 (e.g., via interaction of threads), the lock screw 40 applies a downward force to the cross-bar 30 positioned in the cross-bar slot 70. Because the compliant bending zone 120 is located between the cross-bar slot 70 and the spinal rod slot 60, and as the cross-bar 30 is forced downward, the cross-bar 30 applies a force to the snap-fit members 90A, 90B which clamp inward on the spinal rod 20 in the spinal rod slot 60. In various implementations, the aperture 130 and/or thinned section 140 enables greater flexion in the compliant bending zone 120 than in other sections of the connector 10. Accordingly, as force is applied by the lock screw action, the compliant bending zone 120 flexes (or, bends) to translate the downward force from the lock screw 40 into clamping force at the spinal rod slot 60.

In particular implementations, such as in implementations illustrated in FIGS. 1-4, the cross-bar slot 70 is exposed at a top 150 of the connector 10. In such cases, the cross-bar slot 70 is defined by distinct walls (or, wings) 160 that oppose one another and are not connected at the top 150 of the connector 10. The walls 160A, 160B can include internal threads defining the lock screw slot 80 (over the cross-bar-slot 70). In these cases, the cross-bar 30 can be loaded in the cross-bar slot 70 from the top 150 of the connector 10 (e.g., through the lock-screw slot 80) in the second engagement direction ($D_{e2}$). In certain of these implementations, the connector 10 can include at least one locking flange 170 at the lock-screw slot 80 for engaging the cross-bar 30 in the cross-bar slot 70. In various implementations, a plurality of threads in the lock-screw slot 80 include a locking flange 170, e.g., helical flange threads, that help to prevent splay between walls 160 and corresponding bending at the cross-bar slot 70. That is, the locking flanges 170 can engage lock screw threads 172 on lock screw 40 (FIG. 4) to prevent splaying (or, radial tilt) of the walls 160 relative to the lock screw 40. In certain cases, locking flanges 170 and lock screw threads 172 include complementary ridges, or hooks, that are configured to provide resistance across two faces, e.g., as in complementary multi-face ridges. The interaction between locking flanges 170 and lock screw threads 172 can aid in maintaining a radial position (relative to axial lock screw motion) of the walls 160 in an open (or, exposed) cross-bar slot configuration such as illustrated in FIGS. 1-4 and 9-13.

In additional implementations, such as example connector 10A illustrated in FIGS. 5-8, the cross-bar-slot 70 is closed at the top 150 of the connector 10A. In these cases, an annular member 180 can define the lock screw slot 80, such that the cross-bar 30 can only be loaded into or out of the slot 80 from one of the slot openings 190. In particular examples, the cross-bar slot 70 is non-circular. For example, the cross-bar slot 70 can have a rounded rectangular cross-sectional shape in a direction perpendicular to the second engagement direction ($D_{e2}$), as illustrated in particular clarity in FIGS. 5 and 7. In some cases, the cross-bar slot 70 is shaped to accommodate a cross-bar 30 that is non-circular in cross-sectional shape, e.g., a rounded rectangle, or oblong cross-sectional shape. Certain examples of such cross-bars 30 are illustrated in FIGS. 14-17.

In some implementations, the body of the connector 10 (and/or 10A) is a monolithic piece of material. In such examples, the body of the connector 10 can include a unitary piece of metal or composite. In other cases, the connector 10 (and/or 10A) has a body that includes a plurality of distinct components. In one example, as illustrated in FIGS. 9-13, a connector 10B includes a plurality of distinct components. For example, the connector 10B can include a main body 200 defining a spinal rod slot 60, cross-bar slot 70, and lock screw slot 80 as described with respect to connector 10A. In these implementations, the spinal rod slot 60 is further defined by an insert 210 configured to couple with the snap-fit members 90A, 90B. The insert 210 can include a collet, such as a spherical collet. In certain implementations, the insert 210 extends from a lower portion of the cross-bar slot 70 into the spinal rod slot 60, such that the cross-bar 30 contacts the insert 210 when the connector 10B is locked, e.g., so that the cross-bar 30 applies a locking force on the insert 210. In other implementations, the insert 210 is located entirely below the cross-bar slot 70 (between snap-fit members 90A, 90B), such that when inserted, the cross-bar 30 does not contact the insert 210. In these cases, the insert 210 is retained in the spinal rod slot 60 by the clamping force of the snap-fit members 90A, 90B. In various implementations, the insert 210 includes an arcuate member with a spherical outer surface 220 that is configured to pivot and rotate within the snap-fit members 90A, 90B. The insert 210 may be configured to allow one or more degrees of freedom for accommodating distinct spinal rod angles, e.g., when the connector 10B is unlocked. In various implementations, the insert 210 allows for off-axis positioning of the connector 10B relative to the spinal rod 20, e.g., by modifying the first engagement direction ($D_{e1}$) relative to the second engagement direction ($D_{e2}$). In some cases, the snap-fit members 90A, 90B can include at least one flat (or planar section) 230 that is configured to interface with the spherical outer surface 220 of the insert 210 and limit movement of the insert 210. In certain cases, the insert 210 further includes at least one flat (or planar section 232) that is configured to limit movement of the insert 210 relative to the snap-fit members 90A, 90B. In various implementations, the insert 210 includes at least one lip 240 on an arm 250 configured to retain the spinal rod 20, e.g., in a snap-fit connection. Similarly to connectors 10 and 10A, the connector 10B may be configured to enable simultaneous locking of both the spinal rod 20 in the spinal rod slot 60 (e.g., in insert 210) and the cross-bar 30 in the cross-bar slot 70 with a single lock screw action.

FIGS. 14-17 illustrate views of cross-bar 30 according to certain implementations. In these examples, the cross-bar 30 is sized to span across the spinal midline 50 of a patient (FIGS. 18, 19), and includes a body 260 having a fixation section 270 and a loading section 280 removably coupled with the fixation section 270. In certain cases, the loading section 280 is removable after the fixation section engages a set of tulip rod connectors 10 (or, 10A, 10B) on opposite sides of the spinal midline 50. In other cases, the loading section 280 remains with the fixation section 270 after securing the cross-bar 30 into the connectors 10. In various implementations, the cross-bar 30 is one of a set of (e.g., two or more) cross-bars that span between distinct spinal rods 20 positioned on opposite sides of the spinal midline 50. In some cases, the body 260 can include a break zone 290 between the fixation section 270 and the loading section 280 for enabling removal (e.g., snap-off or twist-off removal) of the loading section 280.

As illustrated in FIGS. 14-17, the fixation section 270 has a longitudinal axis (Auf) that is aligned with an insertion direction (e.g., first engagement direction $D_{e1}$) across the spinal midline 50. The fixation section 270 may have a cylindrical cross-sectional shape in some cases. In other cases, the fixation section 270 has a non-cylindrical cross-sectional shape 300, e.g., as illustrated in FIGS. 14-17. In some examples, the non-cylindrical cross-sectional shape 300 includes at least one of: an ellipse, a rounded rectangle, or a tapered rectangle. In some cases, the fixation section 270 is sized to fit in a cross-bar slot 70 in each of the tulip rod connectors 10 (or, 10A, 10B) with clearance to enable coupling between tulip rod connectors 10 that are misaligned in at least one of an X direction, Y direction, or Z direction. That is, an outer dimension of the fixation section 270 can be undersized relative to the inner dimension of the cross-bar slot 70 to enable alignment adjustment of the cross-bar 30 when placed in the slot 70. In certain examples, a tip 310 of the fixation section 270 is tapered or pointed.

Figure 16:
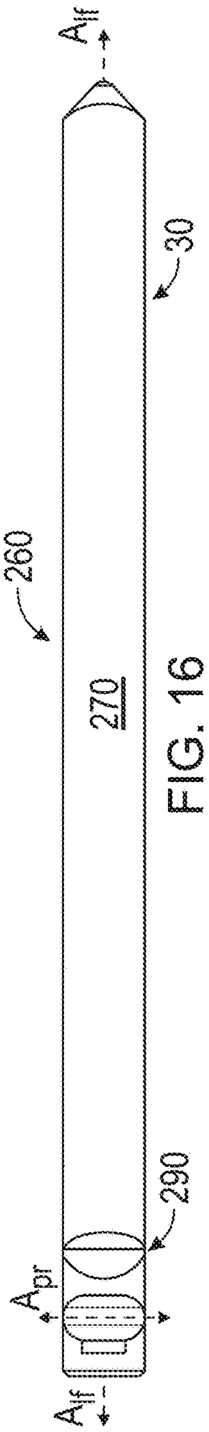
Figure 17:
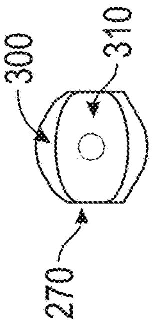

In further examples, the fixation section 270 is bendable and/or rotatable. In a particular example, the fixation section 270 includes a section 320 having a reduced cross-sectional dimension (also called a "bend zone") to aid in at least one of bending or rotating. The fixation section 270 can also be configured to bend and rotate in-situ (e.g., at section 320). According to certain implementations, the loading section 280 includes a recess 330 for engaging a reducer tool 332 (FIG. 18). In certain cases, the recess 330 has a primary axis ($A_{pr}$) that is perpendicular to a longitudinal axis (Auf) of the fixation section 270 (FIG. 16). In particular examples, an outer dimension of the loading section 280 is larger than an outer dimension of the fixation section 270 in at least one direction (e.g., in a direction perpendicular to $A_{pr}$).

Various implementations include devices, systems, and related approaches for percutaneous posterior fixation on a patient. For example, viewed in the context of FIGS. 18 and 19, approaches can include inserting and connecting a cross-bar (e.g., cross-bar 30) across a spinal midline 50 with incisions on either side of the spinal midline 50. In some cases, the approaches include connecting the cross-bar 30 to a first tulip rod connector 10 on a first side of the spinal midline 50 and a second tulip rod connector 10 on a second side of the spinal midline 50. In certain examples, inserting and connecting the cross-bar 30 is performed without any incision (e.g., external incision) through the spinal midline 50 of the patient. In more particular cases, inserting and connecting the cross-bar 30 is performed with only two incisions, one on each side of the spinal midline 50 of the patient. In certain of these cases, inserting and connecting the cross-bar 30 is performed with a lateral, subcutaneous insertion across the spinal midline 50. As described herein, the cross-bar 30 and a corresponding spinal rod 20 can be secured in the connector 10 with a single lock screw action, e.g., by tightening the lock screw 40 to fully engage the threads on the lock screw slot 80. The connector 10 enables numerous variations on approaches for percutaneous posterior fixation on a patient, certain examples of which are described herein. With reference to FIGS. 18 and 19, in certain implementations, a reducer tool 332 (e.g., reducer tower) can be used for coupling a connector 10 to a spinal rod 20. In various implementations, a rod inserter 334 can be used to insert the cross-bar 30 across the spinal midline 50, e.g., to connect with tulip rod connectors 10 on either side of the midline 50. In additional implementations, or in complementary scenarios, a piledriver reducer 336 can be used to aid in securing the lock screw 40 in the lock screw slot 80, e.g., to secure cross-bar 30 and spinal rod 20 in the connector 10. In additional optional implementations, forceps can be used to aid in guiding the cross-bar 30 through the patient's spinal process and/or intra-spinous ligaments.

FIGS. 20-22 are flow diagrams illustrating processes in methods of percutaneous posterior fixation.

FIG. 20 is a flow diagram illustrating processes in a method of percutaneous posterior fixation on a patient according to some implementations. With continuing reference to FIGS. 18 and 19, the method can include the following processes:

- P1: coupling a first tulip rod connector 10 to a first spinal rod 20 on a first side of the spinal midline 50 of the patient,
- P2: coupling a second tulip rod connector 10 to a second spinal rod 20 on a second side of the spinal midline 50 of the patient,
- P3: inserting a cross-bar 30 in a first cross-bar slot 70 in the first tulip rod connector 10,
- P4: inserting the cross-bar 30 in a second cross-bar slot 70 in the second tulip rod connector 10,
- P5: securing the cross-bar 30 with a first lock screw 40 in the first tulip rod connector 10, and
- P6: securing the cross-bar 30 with a second lock screw 40 in the second tulip rod connector 10.

FIG. 21 is a flow diagram illustrating processes in a method of percutaneous posterior fixation on a patient according to some implementations. With continuing reference to FIGS. 18 and 19, the method can include the following processes:

- P101: coupling a first tulip rod connector 10 to a first spinal rod 20 on a first side of the spinal midline 50 of the patient, the first tulip rod connector 10 including a first cross-bar slot 70,
- P102: inserting a cross-bar 30 in a second cross-bar slot 70 in a second tulip rod connector 10 on a second side of the spinal midline 50 of the patient,
- P103: coupling the second tulip rod connector 10 to a second spinal rod 20 on the second side of the spinal midline 50 of the patient,
- P104: inserting the cross-bar 30 in the first cross-bar slot 70 in the first tulip rod connector 10,
- P105: securing the cross-bar 30 with a first lock screw 40 in the first tulip rod connector 10, and
- P106: securing the cross-bar 30 with a second lock screw 40 in the second tulip rod connector 10.

FIG. 22 is a flow diagram illustrating processes in a method of percutaneous posterior fixation on a patient according to some implementations. With continuing reference to FIGS. 18 and 19, the method can include the following processes:

- P201: coupling a first tulip rod connector 10 to a first spinal rod 20 on a first side of the spinal midline 50 of the patient,
- P202: coupling a cross-bar 30 in a first cross-bar slot 70 in the first tulip rod connector 10,
- P203: securing the cross-bar 30 in the first tulip rod connector 10 with a first lock screw 40,
- P204: coupling a second tulip rod connector 10 to a second spinal rod 20 on a second side of the spinal midline 50 of the patient,
- P205: coupling the cross-bar 30 to a second cross-bar slot 70 in the second tulip rod connector 10, and
- P206: securing the cross-bar 30 in the second tulip rod connector 10 with a second lock screw 40.

In some of these examples, securing the cross-bar 30 in the first tulip rod connector 10 is performed prior to coupling the second tulip rod connector 10 to the second spinal rod 20 on the second side of the spinal midline 50. In various implementations, coupling the first tulip rod connector 10 to the first spinal rod 20 and coupling the cross-bar 30 in the first cross-bar slot 70 is performed with a reducer tool 332, such as a reducer tower (FIG. 18). The reducer tool 332 can be configured to engage the first tulip rod connector 10 and the cross-bar 30 in a direction perpendicular to a direction of the first spinal rod 20. In certain examples, another reducer tool (e.g., a rod inserter 334) is configured to pass the cross-bar 30 from the first side of the spinal midline 50 to the second side of the spinal midline 50.

As noted herein, minimally invasive percutaneous posterior fixation procedures have conventionally presented challenges to medical professionals. For example, it is challenging to place cross-bars or cross-connectors between spinal rod connectors (e.g., across the spinal midline) in a minimally invasive manner. It can be difficult to navigate a cross-bar through soft tissue and the spinal structure, especially with the limited sightlines available in a percutaneous procedure. Accordingly, many conventional approaches use one or more incisions across the patient's midline to improve visualization of the soft tissue and spinal structure. Certain of these challenges are described in U.S. Pat. No. 9,610,104 ('104 patent), which is hereby incorporated by reference in its entirety. In contrast to the revision system and extender construct described in the '104 patent, the various disclosed implementations can be beneficially deployed in an initial construct procedure (as well as in a revision procedure). Further, the disclosed implementations enable securing both a spinal rod and a cross-bar with a single lock screw action, significantly improving the efficiency of the cross-midline connection. As noted herein, the various disclosed implementations can enable a minimally invasive percutaneous spinal fixation procedure. In addition to enabling a minimally invasive percutaneous spinal fixation procedure, the disclosed implementations can enable assembly of a fixation construct in-situ, improving the efficiency of the procedure and consequently reducing surgical time and associated risk.

In various implementations, components described as being "coupled" to one another can be joined along one or more interfaces. In some implementations, these interfaces can include junctions between distinct components, and in other cases, these interfaces can include a solidly and/or integrally formed interconnection. That is, in some cases, components that are "coupled" to one another can be simultaneously formed to define a single continuous member. However, in other implementations, these coupled components can be formed as separate members and be subsequently joined through known processes (e.g., soldering, fastening, ultrasonic welding, bonding). In various implementations, electronic components described as being "coupled" can be linked via conventional hard-wired and/or wireless means such that these electronic components can communicate data with one another. Additionally, sub-components within a given component can be considered to be linked via conventional pathways, which may not necessarily be illustrated.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated. As used in this specification and the claims, unless otherwise stated, the term "about," "approximately," "generally," and "substantially" refers to variations of less than or equal to +/−1%, +/−2%, +/−3%, +/−4%, +/−5%, +/−6%, +/−7%, +/−8%, +/−9%, +/−10%, +/−11%, +/−12%, +/−14%, +/−15%, +/−16%, +/−17%, +/−18%, +/−19%, or +/−20%, depending on the embodiment. As a further non-limiting example, about 100 millimeters represents a range of 95 millimeters to 105 millimeters, 90 millimeters to 110 millimeters, or 85 millimeters to 115 millimeters, depending on the embodiments.

While inventive features described herein have been described in terms of preferred embodiments for achieving the objectives, it will be appreciated by those skilled in the art that variations may be accomplished in view of these teachings without deviating from the spirit or scope of the invention. Also, while this invention has been described according to a preferred use in spinal applications, it will be appreciated that it may be applied to various other uses desiring surgical fixation, for example, the fixation of long bones.

A number of implementations have been described. Nevertheless, it will be understood that additional modifications may be made without departing from the scope of the inventive concepts described herein, and, accordingly, other implementations are within the scope of the following claims.

We claim:

1. A tulip rod connector assembly, comprising:
a tulip rod connector comprising:
a pair of clamping members facing each other and defining a spinal rod slot, the spinal rod slot having a first engagement direction;
a cross-bar slot having a second engagement direction that is distinct from the first engagement direction; and
a lock screw slot adjacent to the cross-bar slot, wherein the cross-bar slot is open to the lock screw slot such that the lock screw slot is defined by two opposing wings,
wherein the tulip rod connector enables locking of both a spinal rod in the spinal rod slot and a cross-bar in the cross-bar slot with a single lock screw action;
a spinal rod, the spinal rod configured and dimensioned to be received in the spinal rod slot; and
a cross bar, the cross bar having at least one flat extending along a length of the cross bar and being configured and dimensioned to be received in the cross-bar slot;
wherein the tulip rod connector further includes first and second compliant bending zones associated with the respective clamping members, and disposed between the clamping members and the opposing wings, each compliant bending zone being curved and tapering inwardly and outwardly such that a downward force on the cross bar from the lock screw causes both the first and second compliant bending zones to bend to provide a clamping force to the pair of clamping members.

2. The tulip rod connector assembly of claim 1, wherein the cross-bar slot is oversized relative to the cross-bar to enable at least one of: off-axis positioning of the cross-bar, or engagement with a plurality of distinct cross-bars having distinct outer dimensions.

3. The tulip rod connector assembly of claim 1, wherein the spinal rod slot enables a pressure-fit connection between the tulip rod connector and the spinal rod.

4. The tulip rod connector assembly of claim 1, wherein the spinal rod slot is defined by a set of snap-fit members.

5. The tulip rod connector assembly of claim 1, wherein the cross-bar slot is exposed at a top of the tulip rod connector.

6. The tulip rod connector assembly of claim 5, wherein the tulip rod connector further comprises a locking flange for engaging the cross-bar in the cross-bar slot.

7. The tulip rod connector assembly of claim 1, wherein each of the compliant bending zones is located adjacent to the spinal rod slot and the cross-bar slot.

8. The tulip rod connector assembly of claim 7, wherein the compliant bending zone translates at least a portion of a downward force from the single lock screw action at the lock screw slot into a clamping force on the rod slot.

9. The tulip rod connector assembly of claim 7, wherein the compliant bending zone is defined by at least one of an aperture or a thinned section.

10. The tulip rod connector assembly of claim 1, wherein the second engagement direction is approximately perpendicular to the first engagement direction.

11. The tulip rod connector assembly of claim 1, wherein a body of the tulip rod connector is a monolithic piece of material.

12. The tulip rod connector assembly of claim 1, wherein a body of the tulip rod connector includes a plurality of distinct components, including a main body and a collet at least partially defining the spinal rod slot.

13. The tulip rod connector assembly of claim 1, wherein a width of the spinal rod slot is larger than a width of the cross-bar slot.

14. The tulip rod connector assembly of claim 1, wherein the cross-bar slot is non-circular.

15. The tulip rod connector assembly of claim 14, wherein the cross-bar slot has a rounded rectangular cross-sectional shape in a direction perpendicular to the second engagement direction.

* * * * *